United States Patent [19]

Lemelson

[11] Patent Number: 4,578,061
[45] Date of Patent: Mar. 25, 1986

[54] INJECTION CATHETER AND METHOD

[76] Inventor: Jerome H. Lemelson, 85 Rector St., Metuchen, N.J. 08840

[21] Appl. No.: 636,239

[22] Filed: Jul. 31, 1984

Related U.S. Application Data

[63] Continuation of Ser. No. 201,531, Oct. 28, 1980, which is a continuation-in-part of Ser. No. 885,263, Mar. 10, 1978, abandoned.

[51] Int. Cl.$^4$ ............... A61M 5/00; A61M 25/00
[52] U.S. Cl. ............................. 604/164; 604/198
[58] Field of Search ..................... 604/51-53, 604/55, 117, 144, 164-169, 192-198, 263

[56] References Cited

U.S. PATENT DOCUMENTS

| | | | |
|---|---|---|---|
| 3,380,448 | 4/1968 | Sadove et al. | 604/263 |
| 3,406,687 | 10/1968 | Moyer | 604/192 X |
| 3,598,119 | 8/1971 | White | 604/164 X |
| 3,659,610 | 5/1972 | Cimber | 604/198 X |
| 3,675,651 | 7/1972 | Meyer | 604/144 |
| 4,136,695 | 1/1979 | Dafoe | 604/198 X |

Primary Examiner—Dalton L. Truluck

[57] ABSTRACT

A catheter and method are provided for injecting a quantity of a liquid, such as a medication, into tissue located immediately adjacent the head of the catheter. A hollow needle such as a hypodermic needle, is movably supported within the head of the catheter and is urged longitudinally through a passageway therein to protrude outwardly from the catheter head after the catheter is selectively located within a body duct. The needle penetrates tissue adjacent the head and a liquid is flowed thereafter through and out the end of the needle into the tissue. The needle may be moved longitudinally through a passageway extending along or parallel to the longitudinal axis of the catheter and head or may be moved longitudinally and laterally through the head to protrude from a sidewall portion thereof at an angle to the body duct into which the head is inserted and in a manner to penetrate the tissue of the duct or an organ disposed adjacent the head. Control of the catheter, needle movement through the head and flow of a liquid through and from the end of the needle, are affected from outside of the body.

8 Claims, 6 Drawing Figures

INJECTION CATHETER AND METHOD

RELATED APPLICATIONS

This is a continuation of copending application Ser. No. 201,531 filed Oct. 28, 1980 which was a continuation-in-part of Ser. No. 885,263 filed Mar. 10, 1978, now abandoned.

SUMMARY OF THE INVENTION

This invention relates to a medical device, such as a probe, catheter or similar device which is adapted to be inserted into a living being through a cavity therein, such as a vein or artery, and manipulated so as to provide an operating head of the catheter located at a selected position within the body. Thereafter mechanical or fluidic means is employed to project a hypodermic needle from a retracted position within the head to an extended position beyond the head whereby tissue located adjacent the head is penetrated by the end of the needle. After such penetration is affected, a liquid is forced through the needle to flow into the tissue penetrated by the needle.

Most medications are applied to living beings either by ingestion through the mouth or by means of a hypodermic needle penetrating the skin wherein a liquid is passed through the needle under pressure and caused to enter body tissue from which it flows into the bloodstream. It is evident that such techniques require overdosing and subject the body of the patient to the medication injected or ingested before one or more desired locations within the body are reached by the medication in its circulation through the bloodstream.

By means of the instant invention, a small quantity of a liquid medication such as an antibiotic, sulfer drug, chemical agent or the like is injected at a select location within the body, such as a particular portion of a body duct or organ, a tumor or the like through a needle which is disposed at such location by means of a catheter. The needle is normally retracted in the device so that it will not penetrate tissue as the device is worked through the body duct and is projected therefrom, either by direct mechanical shaft coupling to the needle or by means of fluid pressure applied to the needle or a piston connected to the needle through a flexible tube such as the flexible tube forming the catheter.

Accordingly it is a primary object of this invention to provide a new and improved apparatus and method for injecting a predetermined quantity of a drug into a human body.

Another object is to provide an improved apparatus and method for injecting a select quantity of a drug into tissue located deep within a human being, without penetrating the skin and other tissue extending to such location.

Another object is to provide new and improved structures in catheters operable to inject select quantities of medications and drugs deep within a living being after the catheter has been selectively located within the living being.

Another object is to provide an injection catheter which may be employed to inject a liquid material into human tissue located within the human body without the need to create an incision in the skin of the person receiving such treatment.

Another object is to provide a catheter device for injecting a fluid into internal human tissue by means of a needle which is controllably projectable from the end of a catheter.

With the above and such other objects in view as may hereinafter more fully appear and a study of the accompanying specification and drawings, the invention consists of the novel constructions and combinations of parts as will be more fully described hereafter, but it is to be understood that changes and modifications may be resorted to without departing from the spirit and nature of the invention as claimed:

DESCRIPTION OF THE DRAWINGS

In FIG. 1 is shown a first form of the invention comprising an assembly 10 formed of an elongated flexible hollow tube 31 made of a flexible plastic such as an elastomeric polymer or rubber and connected at one of its ends to an actuating device 11 which may be manually operated for urging the longitudinal movement of a flexible shaft 30 in the flexible tube 31, the combination defining what will be referred to hereafter as an ejection catheter. Depression of an actuator head or push button 20 by the movement of the human thumb thereagainst while a flange 12 forming part of the actuating device 11 is held by the fingers of the hand, urges shaft 30 longitudinally through the tube 31. The other end of tube 31 is inserted into a bore or opening 35 in a head or fitting 32 located at the end of the catheter, while fitting is an elongated bead-like hollow housing not much greater in diameter than the tube 31 and serving as a retainer and guide for a device or quantity of solid material to be implanted into the tissue adjacent said head when the latter is disposed at a given location in a body duct, such as an artery, the intestine, throat or other body duct. Fitting 32 has a tapered forward end 33 and a chamber defined by a cavity 34 of constant diameter extending from the end 33 thereof, into which chamber a piston 36 is slidably movable and is connected to the end of flexible shaft 30. Material, such as a medication in the form of a pill or solid cylinder 37, a viscous fluid such as a cream or salve, or a container for medication, is disposed within the chamber or cavity 34 in such a manner that it is normally retained therein but will be ejected from the end of the fitting when the piston 36 is urged forwardly by the forward movement of shaft 30. The material or pill 37 may be frictionally, adhesively or otherwise retained in chamber 34 so as to hold it therein until it is urged out of the operating end of head 32.

Figure 1:
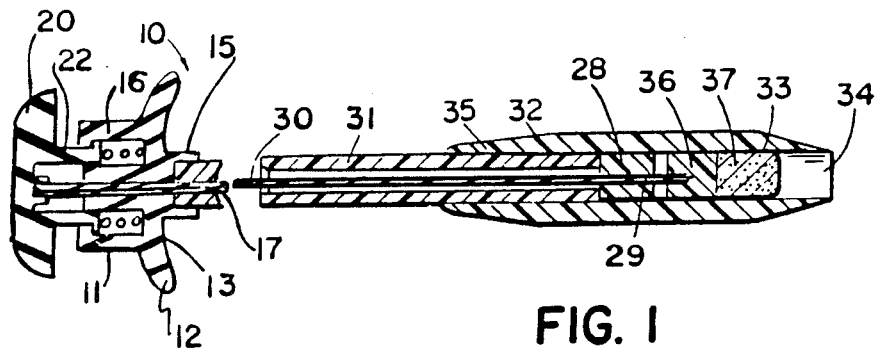
FIG. 1 is a side view in cross section of both ends of an elongated medical catheter having means for carrying and ejecting a solid material from its operating head or end.

The actuating device 11 comprises a hollow tubular body 16 connected to the finger grip 13, through which body the flexible shaft 17 extends to the tubular retaining means 22 of the pushbutton head 20. When head 20 is pushed forwardly by the force applied by thumb thereagainst while fingers hold the grip 13, the push-pull shaft 30 is urged forwardly through the flexible tube 31 and the piston 36 which is connected to the end of said shaft, is thereby urged forwardly in the cavity or chamber 34 so as to force the device or medication 37 which is disposed against or forwardly of the piston, out of the end of the fitting 32 and preferably, although not necessarily, completely from the end of said fitting so as to dispose the device 37 adjacent to tissue which surrounds or is adjacent the head or fitting 32.

The end of flexible tube 31 is adhesively bonded or welded to the tapered rear end 35 of the head end or fitting 32 of the catheter and is shown abutting a cylindrical plug 28 containing a passageway 29 extending axially therethrough which serves as a lineal bearing in which the flexible shaft 30 may be longitudinally driven forwardly and rearwardly to urge the piston 36 to which it is connected, both forwardly and rearwardly. A helical spring 20S is shown disposed beneath the head 20 and a retaining wall portion 12 of the actuating assembly for normally urging the head 20 outwardly from the actuating end to maintain the piston 36 retracted prior to the ejection of the material 37 from the end of the head 32.

It is noted that a thin plastic film, wax or other material may be disposed across the opening in the cavity 34 of the head portion 32 of the catheter to maintain body fluids out of the passageway 34 until the wax or plastic film has been removed or ruptured by the forward movement of the solid material 37 as urged by piston 36 thereagainst. It is also noted that the finger operated actuating device 11 may be replaced by a pistol grip mechanism containing a trigger which is finger operated and is used to urge the flexible shaft 30 longitudinally in the bore of the flexible cable or tube 31 for the purpose of ejecting the solid material or device 37 from the end of the head 32 or disposing at least a portion of 37 outwardly from the end of the head to engage or otherwise affect tissue within the human body adjacent the head.

Figure 2:
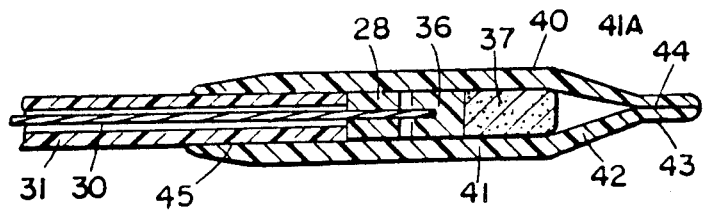
FIG. 2 is a side view in cross section of a modified form of the head end of a catheter of the type shown in FIG. 1 wherein such head contains a flexible wall portion which is normally closed or collapsed into a flat shape and may be opened by forcing a solid material or piston therethrough which material may be ejected from the open end of the expanded portion of the head.
Figure 3:
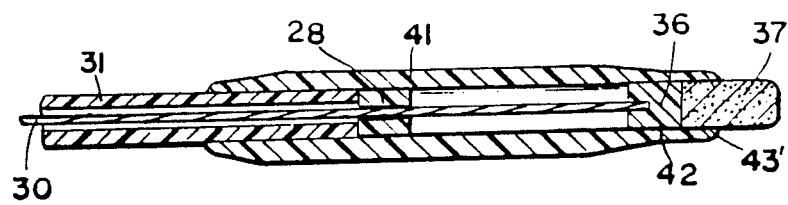
FIG. 3 is a side view in cross section of the device of FIG. 2 showing the solid material thereof being ejected from the end of the catheter.

In a second embodiment illustrated in FIGS. 2 and 3, the head end or fitting 40 of a catheter 39 has a tubular wall 41 having a tapered forward end 42, the end portion 43 of which is collapsed or formed closed, as illustrated, forming interface 44 which is normally in a sealing condition to close off the interior volume 41A until the tapered wall portion 42 is outwardly expanded so as to separate the interface 44 as illustrated in FIG. 3. When a piston 36 is urged forwardly by the forward movement of flexible shaft 30, it urges the solid cylindrical device or pill 37 through the tapered section 42 and the collapsed section 43 to either position it as illustrated in FIG. 3 protruding from the end of the end portion of the fitting 41 or to eject it completely therefrom so that it lies against the tissue adjacent the end of the catheter. Solid pill 37 may comprise or contain a drug for trea-tissue or may contain a radioactive element and may serve as a source of radiation located, when dispensed from the head of the catheter as described, immediately adjacent a tumor or malignancy for treatsame with such radiation. As provided in FIG. 1, the flexible pushpull shaft 30 is moved longitudinally in a flexible tube which is sealed within the rear portion of the bore of fitting 40 against the rear face of a thrust bearing or plug 28 and secured at its end to the piston 36 as described above. When the piston 36 is retracted to the position illustrated in FIG. 2, the memory of the plastic causes the outwardly expanded end 42 of the fitting 40 to collapse and assume the condition illustrated in FIG. 2 after which the catheter may be removed from the cavity or artery, sterilized and have a new device or plug of material 37 inserted therein for its next use.

The embodiment of FIGS. 2 and 3 as well as that of FIG. 1 may also contain one or more light pipes or fiber optic bundles extending along or within the flexible shaft 30 and through the pistons 36 to serve one or both of two functions, as conductors and receivers of light for observation o sensing the condition of tissue adjacent the end of the piston when projected from the end of the catheter head and/or as a conductor of light such as laser light which may be employed to perform surgery by vaporizing, cutting, burning or corterizing tissue or bone disposed adjacent to or in contact with the projected and exposed end of the piston. Light from an external source such as a laser may be piped through one light pipe or bundle and directed from the end of the piston which may comprise a lens for directing or focusing such light and reflections thereof from tissue or bone may be received by such lens or the end of the other light pipe and passed back along the cather for use in observing the tissue or bone by conventional means.

Figure 4:
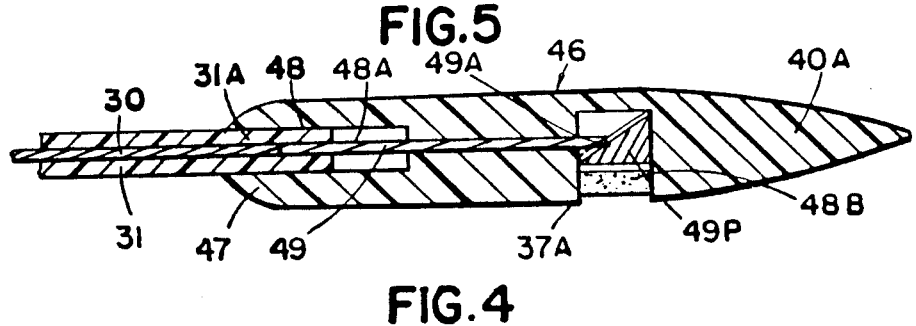
FIG. 4 is a side view in cross section of a modified form of the invention of FIG. 1 wherein a solid material is ejected from the side of the head of the catheter.

In FIG. 4, details are shown of a medical catheter assembly having a head or end fitting 46 with a tapered front end 46A and a rear portion 47 containing a cylindrical bore or cavity 48 extending therein from the rear end and in which the end 31A of a flexible catheter tube 31 is inserted and adhesively sealed or secured by heat sealing to the wall of the head 46. Longitudinally extending through the passageway in the flexible tube 31 is a flexible push-pull shaft 30 which also extends through an extension 48A of the bore 48, in which it is slidably engaged, and from which extension the end of shaft 30 protrudes and engages the rear face of a piston 49T which is adapted to be urged by the forward motion of the shaft 30 longitudinally through a bore 49 which extends normal to the axis defined by the shaft 30 and bore 48. A plug or pill 48B is secured within the bore 49 beneath the outer surface of the head 46 and may be urged by the lateral movement of the piston 49P, outwardly from said bore to be ejected against tissue disposed adjacent the head 46 for the purposes described above. In other words, the end of flexible shaft 30, or an extension thereof, slideably engages or engages in a cavity in the tapered rear face of the piston 49P and when the shaft 30 is urged against the rear face of the piston 49P, it causes the piston to move laterally outwardly through the bore so as to eject the solid pill or material 48B therefrom.

Figure 5:
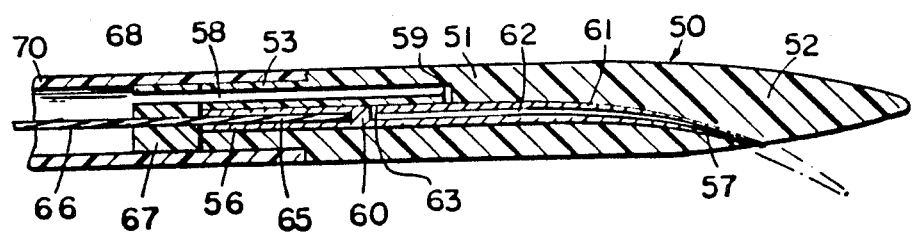
FIG. 5 is a side view in cross section of a modified form of the invention showing means for partially ejecting a hollow needle from the end of the catheter to cause it to be inserted into and through tissue located adjacent the end of the catheter.

In FIG. 5 is shown another form of the invention comprising a catheter having a head assembly 50 at one end thereof which includes a fitting or housing 51 having a tapered forward end 52 as shown and a rear end portion 53 of reduced diameter for frictionally retaining the end of a flexible plastic tube 70 thereagainst. Means are provided at the other end of flexible catheter tube 70 for applying fluid under pressure to the passageway defined by the flexible tube 70 and then to a passageway 58 in the head 51 which latter passageway extends to the surface of a curved needle 60 having a curved head end 61 and a radial bore 63 extending to the interior passageway 62 of the needle 61.

The bore 56 through which the needle 61 extends, has a curved forward end portion 57 which is adapted to receive the curved forward end 61 of the needle 60 and to permit same to be urged therethrough beyond the side of the tapered side wall portion 52 of the head 51 of the catheter. If the needle 61 is formed of a spring-like material, such as a small diameter stainless steel needle, it may be arcuately deformed in the passageway 56 to permit it to conform to the curved forward section 57 thereof and to be partially ejected from the tapered end portion 52 of the head 51 so as to permit a fluid, such as a medication liquid, introduced into the interior volume of the tube 70, to flow through passageway 58 and then through a radially extension 59 thereof to an opening 63 in the side wall of the needle 61 whereafter the fluid may be flowed through the longitudinal opening 62 in the needle 61 and out the end thereof when the latter is suitably positioned within tissue immediately adjacent the cavity into which the head end 51 of the catheter has been inserted. While the tapered housing 51 of head 50 may be formed of metal such as stainless steel or rigid plastic, it may also be formed of a flexible plastic such as polyurethane resin permitting it to deform somewhat when the needle 61 moves therethrough.

In the embodiment illustrated in FIG. 5, a device, such as that illustrated in FIG. 1 or a pistol grip device is used to finger operate the flexible shaft 66 causing it to engage the end of the needle 61 causing the latter to be partially ejected from the end portion 52 of the head 51 of the catheter. After such location of the needle 61 has been effected, a fluid under pressure may be pumped through the passageway or interior 71 of the flexible catheter tubing 70 and flowed, as illustrated, to the hollow passageway extending through the needle 61 and out the end of said needle for its intended purpose.

While each of the embodiments illustrated in FIGS. 1-5 employs a flexible push-pull shaft 30 extending through the flexible catheter tube 31 for lineally actuating a piston to expell a capsule, quantity of fluent medication or other matter from the end of the catheter head, it is noted that the piston 28 of FIGS. 1-3 or 49P of FIG. 4 may be actuated by fluid pressure applied to the interior of the flexible catheter tube from the other end of the catheter such as by means of a manually operated piston moving a liquid in the tube, pump operation or valve opening to release fluid pressure to the tube. The pistons 36 and 49P may also be moved as described to expell material from the catheter head by means of a miniature motor or solenoid mounted in the head of the catheter and controlled in its operation by means of wires conducting electrical energy along the catheter to the head from a source of such energy such as a battery located exterior of the catheter at ther other end thereof and controlled by means of a manually operated switch forming part of the assembly at the other end.

It is also noted that the shaft 30 may also be rotated in the catheter to effect movement of the piston for expelling the material from the head by means of a suitable helical screw advancing the piston in the head when rotated by the rotating shaft to slowly expell the material from the head and/or advance the needle 61 from the head.

The advancing and/or retracting means for the catheter piston or needle described above may also be a vibrating electrical transducer such as a piezoelectric crystal or solenoid operating when vibrated by electrical energy conducted thereto through wires extending through the catheter tube, a simple lineal travelling mechanism such as an inchworm motor mechanism for advancing the p ston through the catheter head. A bimetallic element mounted in the catheter head may also be employed to advance the piston when the bimetallic element is heated and deflected by electrical resistance heating provided by electrical energy fed to a resistance heater in the heat through wires extending along the inside of the catheter tube from a source of such energy connected to the wires at the other end of the tube.

In yet another from of the invention, the piston in the head of the catheter or a similarly functioning device operable to expel a capsule or quantity of matter from the head as described, may be retained against a compressed spring, such as a coil spring located in the head of the catheter and may be released from such retained position to be forced by the spring along the bore in the head in which it is seated to expel the capsule or matter from the head as described when a miniature latch or retainer is released by fluid pressure applied along the catheter tube or by pushing or rotating the flexible shaft extending along the tube to the head, from the other end of the catheter.

It is further noted that the arrangement illustrated in FIG. 5 wherein a needle is projected from the catheter head to inject fluid into tissue adjacent the head, may be employed to effect surgery with respect to tissue adjacent the head by heating and/or cooling the needle or a modified form thereof before and/or after it is extended from the catheter head. Heating may be effected by resistance heating means located in the head and energized by electrical energy conducted to the heat through wires extending from the other end of the catheter and cooling by means of liquid nitrogen or other cryogenic liquid at low temperature which is pumped or pressure forced along the catheter tube from the other end thereof after the needle or otherwise shaped implement is projected from the head of the catheter adjacent tissue or bone to be so operated on.

In yet another form of the invention, laser light at sufficient intensity to corterize or otherwise heat tissue or a surgical blade or tool may be generated and directed along one or more light pipes or fiber optical bundles extending through the center of the catheter tube and either applied directly to tissue adjacent the head through a lens or optical devices which is located at the end of the head fixed or movable therefrom as desriibed to permit the light energy to be properly directed into or toward tissue adjacent the head. If the fitting is a needle which is a light pipe or conductor, it may be inserted into tissue adjacent the head when it is moved from the head as described and may thereafter conduct intense light energy into the tissue into which it is inserted. The needle 61 of FIG. 5, for example, may comprise a solid or hollow needle-like member made of light conducting glass or ceramic material with the tapered end thereof adapted to penetrate tissue when it is projected from the head 51 as described. The flexible actuating cable 66 may comprise a glass or plastic filament or a bundle of such filaments clad with higher refractive index material to define a light conductor for laser light energy directed from a laser into the end thereof which is exterior of the body into which the catheter is inserted wherein the laser light is operable to heat the tip or end of the needle or a metal fitting secured thereto for surgical purposes with respect to tissue into which the end of the needle is inserted as described. The laser light energy may also be directed from the end of the needle into tissue into which the needle is inserted and penetrates. A flexible multiple strand metal wire combined with one or more light pipes or fiber optical bundles extending along the core of the wire, parallel thereto exterior thereof or spirally wound around said core may also be employed to conduct laser light energy to the needle or surgical tool 61 when it is projected from the head 51 of the catheter to heat the end of the needle or a metal fitting secured thereto to a temperature whereby it may be used to cauterize, burn or otherwise affect tissue into which it is inserted or against which it is disposed.

The head 51 of the catheter or the end thereof may also serve as a cauterizing or surgical tool when heated to a temperature whereby it will burn or corterize tissue by laser light energy directed thereagainst from a light pipe or pipes defined by the wire 66 or secured thereto as described above and extending to the rear end of the head or a passageway through the head to near the end thereof to be heated. The end of the head 51 may be shaped as shown in FIG. 5 and may comprise a fitting such as one made of stainless steel or a noble metal such as platenum which will resist corrosion from the high temperature to which it is so heated.

The catheter shown in FIGS. 1-3 may also be modified with all or part of the front portion of the piston 36 or a modified form thereof adapted to be projected from the end of the head in which it is retained while the head is inserted into the body cavity and adapted thereafter to be heated as described above by an electrical resistance heating element disposed therein or laser light energy conducted thereto through a light pipe or pipes connected or coupled to the piston and defining or supported by the actuating cable 30. The piston 36 may comprise a blade, a needle or a plurality of needles made of metal, ceramic or glass and heated as described for corterizing or performing surgical operations with respect to tissue against which or into which it is inserted when the head of the catheter is predeterminately located within the human body. The piston 36 may also comprise or contain a lens or a number of lenses which are optically connected or coupled to the end or ends of the light pipe(s) for viewing tissue adjacent the head by directing viewing light from the other end of the catheter along one light pipe or bundle through the lens to tissue and directing the reflected light back up along another light pipe or bundle to a viewing eyepiece or photoelectric cell or other form of electro-optical monitor such as a video camera. In a similar manner, the piston 49P of FIG. 4 may be similarly heated and constructed as described above for performing surgery and/or cauterization with respect to tissue at the side of the head 46 when laterally projected therefrom as described. Piston 49P may also comprise a blade or otherwise shaped tool or any optical element such as a lens, prism or missor for two way communication as described above with respect to viewing tissue adjacent the side of the head by means of light pipes extending along or within the cable 30, employed to actuate the piston, from a source of light energy and a monitoring device at the other end of the cable.

A catheter employing cryogenics and heating by means of laser light energy or resistence heating means as described may also be employed for combined hot and cold surgery or corterization. For example, after the head or piston or needle is heated as described and employed for surgery, a cryogenic liquid such as liquid nitrogen may be pumped to the head through a passageway in the tubular jacket 31 or 70 to the end thereof and through the head and/or needle or piston and circulated, if necessary by return flow through another passageway in the jacket to perform cryogenic surgery or corterization or to cool the head or tool immediately after it is so heated.

In a modified form of the embodiment of FIG. 5, needle 61 may be replaced with a straight needle which is longitudinally movable in a lineal passageway extending at an angle to the longitudinal axis of the head and opening at the side of the head at the point shown and actuated to move from the opening by the flexible shaft illustrated.

Figure 6:
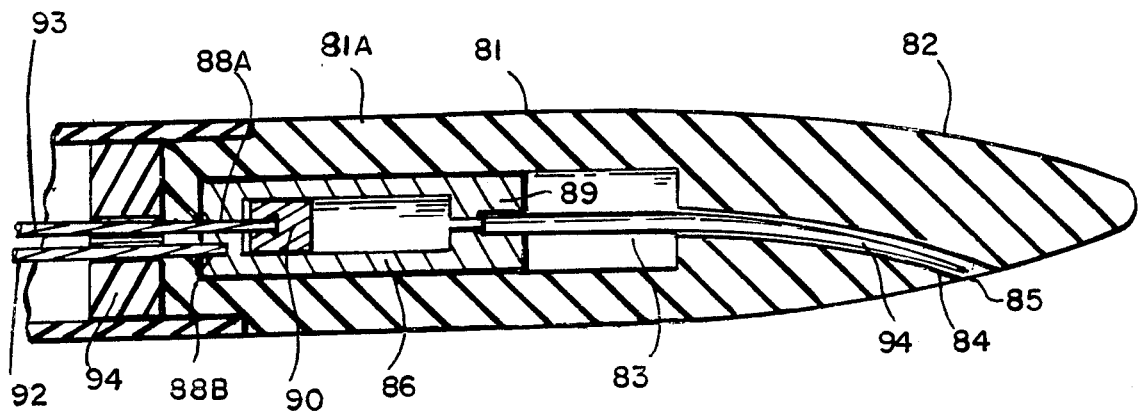
FIG. 6 is a side view with parts broken away and sectioned for clarity of the operating head end of a catheter which is a modified form of the invention illustrated in FIG. 5 and has a hollow needle projectile from an opening in the wall of the head of the catheter.

In FIG. 6 is shown a modified form of injection catheter of the type shown in FIG. 4. The catheter 80 includes an operating head 81 with a smooth tapered end 82 extending from a constant diameter rear portion 81A having a reduced diameter rear portion 83 which is frictionally gripped by and secured to the front end portion of a flexible catheter tube 70A which is a modified form of tube 70 of FIG. 4 in that it accommodates two flexible shafts therein, denoted 92 and 93 which extend the length of such tube 70A from respective manually operated actuating means of the type described wherein both such shafts may be simultaneously urged to move toward the catheter head by hand and one of such shafts, 93, which is operable to effect injection fluid pressurization and flow, may be separately actuated from the other shaft. A constant diameter bore 83 in the rear of the head 80 extends partly through the head and slidably supports a first piston 86 which itself contains a second piston 90 slidable in a bore 87 extending partly through the first piston. A second bore 84 of lesser diameter than bore 83 extends forwardly of bore 83 and curves toward one side of the tapered end 82 of the head to an opening 85. Disposed within the curved passageway 84 is an arcuately shaped hypodermic needle 94 which is secured at its rear end portion within an extension of bore 86 and has its passageway communicating with the remaining volume defined by bore 86 so that liquid medication disposed within the bore 86 may flow into and through the needle to be ejected from the end thereof.

During the movement of the catheter head to a select location in a body duct the needle 94 is retracted as shown in FIG. 6 with its sharp end disposed inward of the opening 88 so that it will not interfer with the forward movement of the catheter to an operating location in the body. When the head 81 is at an operative location within a body duct such as a vein or artery, needle 94 may be caused to move forward through curved bore 84 to project its sharp end outwardly from the sidewall of head 81 so as to penetrate tissue of the body duct in which the head 81 is disposed and/or an organ or other object aligned therewith.

The rear wall 88 of the hollow piston 86 is provided with a central passageway 88A extending therethrough, in which passageway flexible push-pull shaft 93 is slidably movable to permit it to move the sub-piston 90 longitudinally through the bore 87 to force liquid medication therein through the needle 94 when the latter is projected from the opening 85 by the forward movement of piston 86. Such forward movement is effected by urging flexible shaft 92 forward from the other end of the catheter as the end of shaft 92 is secured within a cavity in the endwall 88 of piston 86. A cylindrical plug or disc 94 is secured within the catheter tube or jacket 70B behind the read end wall 81B of the head and contains two passageways or bores extending therethrough for slidably supporting the end portions of the shafts 92 and 93.

During the movement of the catheter through a body duct to position the head 81 at a select location therein prior to projecting the hypodermic needle from the head, piston 86 is disposed retracted in bore 83 while sub-piston 90 is disposed retracted within the interior bore 87 of piston 86 as shown. A select quantity of liquid medication to be injected into tissue or the body duct from the needle is disposed in the volume between the end of the passageway 83 and the endwall 89 of piston 86. When head 81 is properly located, shafts 92 and 93 are urged forward together to selectively project the sharp end of needle 94 beyond opening 85 without flowing liquid therefrom and, upon effecting the desired degree of needle projection, piston 90 is moved forward through passageway 87 by urging shaft 93 forwardly causing part or all of the liquid in volume 87 to be forced through the needle. Adhesives or solvents may be applied to bond the end of sheaving 70A to the rear end of head 81, the shaft 92 to the rear wall 81B of piston 86, shaft 93 to subpiston 90 and the rear end of needle 94 to the front wall 89 of piston 86. Such components as the head 81 and piston 86 may molded of multiple plastic components welded or bonded together.

Other modifications to the constructions illustrated in the drawings are noted as follows:

1. In the embodiment of FIGS. 1-3 a straight hollow tube or needle, such as a hypodermic needle, may be connected to the piston 36 and urged thereby when the piston is longitudinally moved through the head to penetrate the interface 44 and become projected from the end of the head 32 so as to penetrate tissue or bone immediately adjacent the end of the head and/or expell a fluid through such needle when so projected. Such fluid may be conducted under sufficient pressure applied from the other end of flexible tube 31 and through a passageway formed in the piston 36 when the needle is so projected from the end of the heads 32 or 40.

2. The piston 36 of FIGS. 1-3 may be elongated to permit a portion of the free end thereof to protrude from the end of the heads 32 or 40 while the remaining portion of the piston is supported within the end of the head. Such piston may contain one or more electrodes across which electrical energy may be generated such as direct current or alternating current of predetermined voltage and frequency, which current may be applied through fluid in the body duct and/or directly through tissue or bone which said electrodes are made to contact for beneficially affecting such tissue or bone. For example, such electrical energy may be employed to stimulate the growth of tissue or bone adjacent the bone or tissue contacted by or otherwise electrically coupled to the electrodes of the head. The head or fitting 32 or 40 or a portion thereof may also form one electrode or ground for receiving electrical energy from one or more electrodes insulated therefrom on piston 37 when the latter is projected from the end of the head an electrical energy is passed through a cable or wires extending from an external source through the flexible cable 31, along or through the flexible shaft 30.

3. In a modified form of the embodiment described in 2 above, one or more electrodes operable as described may be supported fixed at the end of the head 31 and protruding therefrom or exposed for contact with a body fluid or tissue against which they are urged or in contact with for electrically energizing same as described. One of such electrodes may be disposed at or near the rear end of the head with the other being located at the front end of the head to permit such currect to pass through a substantial portion of tissue adjacent the head when the catheter is properly disposed in a body duct or tissue of a living organism.

4. In the embodiment of FIG. 5 the needle 61 may be electrically connected to a source of electrical energy through a suitable control and energized, as described, when the needle is projected from the head and is penetrating tissue for the purpose of electrically treating such tissue with direct or alternating current. A portion of the head 52 or an electrode disposed thereon and accessible to body fluid or tissue surrounding the head may serve as a ground for electrical energy passing through the tissue from the needle 62.

5. In the embodiment of FIG. 4 the piston 49P may comprise or contain an electrode or electrodes adapted to engage and electrically energize or pass current through tissue such as the wall of a body duct, artery or vein and adjacent tissue when the piston is projected outwardly from the laterall extending bore in which it is movable as described.

6. In all of the embodiments illustrated and described herein, one or more light pipes, such as flexible fiber optical cables or filaments may extend from a viewing means exterior of the catheter at the far end of the flexible tubes 31,70 through or adjacent the described catheter heads or components thereof for providing at a remote location, an image of the tissue or material adjacent the catheter head to permit observation of the tissue to be so operated on or affected as described and/or to provide image information for use or receipt by one or more transducers operable to sense and transduce such information into analyzable electrical signals for diagnostic and control purposes. The light pipe, for example, may extend along the center of or may comprise the flexible shafts 30,66 and may be coupled to a lens or receptor supported by the pistons 36,49P for receiving light directed along one light pipe from a source at the other end of the catheter against tissue adjacent the end of the catheter head or piston and for piping or channelling such light back along the catheter to an external receptor therefore such as view forming optical components or a light-to-electrical energy transducer such as a photodetector.

7. In yet another embodiment of the invention, the heads 32,41,40A and 52 of FIGS. 1-5 and/or the pistons 36,49P may contain embedded therein or wound thereon one or more coils of wire with or without cores and/or other transducers to be energized with electrical energy conducted along the catheter or wires extending along the flexible tube of the catheter when a switch is manually closed or an automatic control operates for inducing electrical current in bone or tissue in the vicinity of such coil when so energized by properly manipulating the catheter to dispose the head thereof and/or the piston adjacent selected tissue or bone to be beneficially affected or destroyed by induced electrical energy when the coil is energized. various operations may be performed to the benefit of a living organism, tissue or bone of a person.

8. A combined coil and electrode arrangement associated with a catheter head or piston, as described, may be employed wherein both the coil and electrodes may be simultaneously or sequentially energized fro inducing currects in tissue or bone and directly flowing electrical energy through same or different adjacent regions of the human body.

9. In all of the embodiments described above, the flexible tubular portion of the catheter which extends to the operating head may be replaced by a rigid tube or needle support therefore.

10. For those embodiments defined above which employ an electrically energized device such as a motor, solenoid, radiation generator or sensor or a plurality of same supported in the operating head of the catheter, the flexible catheter jacket 70 or 70A or a tube flexible tube disposed therein and running the length of the jacket may contain two or more conductors extending along the length thereof and electrically connected at one end to a source of electrical energy and electronic circuitry for processing and analyzing signals generated by the transducer and at the head end to the one or more electrical devices mounted in the head. Such conductors may comprise space separated strip-like portions of the extruded plastic tube made of flexible conducting plastic or polymer and strips of an electrically conducting polymer which are cast, printed or extruded along the inside wall of the flexible tube or between layers of extrusion material forming the tube wall. Such conductors may also be in the form of two or more rounded or cylindrical metal wires or flat metal strips which bonded to the inside surface of the jacket or tube comprising the outer wall of the catheter support line 70 or may be embedded in the wall of such tube and attached at their ends to terminal devices such as connectors or directly to the described electrical device and circuit.

11. A flexible light pipe such as an optical fiber or fiber bundle may be similarly attached to or embedded within the side wall of the jacket or a flexible tube within the catheter jacket for conducting light energy to the head of operating end of the catheter for energizing a solar type cell therein adapted receive light conducted by said light pipe thereto for generating electrical energy for energizing one or more electrical devices or electrodes supported by the catherter head and operable to perform treatment and/or diagnostic functions with respect to a living being in which the device is disposed, such as the treatment of a tumor or disease located adjacent the head of the catheter.

12. Any of the catheter operating heads described may contain a lens or other optical device for receiving image defining light which is either generated by a small electric lamp, directed along a flexible light pipe extending the length of the catheter tube from an external source or generated by a chemical in a reservoir or device inserted in the head and applied to illuminate the tissue or matter immediately adjacent the head in the body or body duct into which the head is inserted wherein such lens is optically coupled to the end of a suitable flexible light pipe extending the length of the catheter tube to a viewing means at the other end of the catheter. Such lens and light pipeviewer combination may be employed to visually monitor tissue or bone adjacent the head before forcing the small quantity of matter from the head, as described, or before projecting the hollow needle from the head and administering the liquid medication therethrough to tissue.

13. The projectile needle of the embodiments of FIGS. 4 and 6 may contain one or more electrodes or replaced with a device containing one or more electrodes adapted to be disposed thereby when the needle or electrode support is projected, as described, against or into tissue or bone and to apply electrical energy generated and conducted thereto from a source external of the body throug conductors extending the length of the catheter tube or from a battery or cell within the head for the purpose of electrically treating or stimulating such tissue or measuring or detecting and physiological variable with a sensing means defined by or associated with the electrode(s).

14. The embodiments of FIGS. 1-3 and 5 may also be employed to implant a drug releasing capsule or container within a body duct which capsule acts to periodically or upon biodegradation, release a quantity or quantities of medication at the location of such capsule. Such capsule may be bonded or otherwise secured to the tissue against which it is so disposed or allowed to remain or work its way along the body duct until it biodegrades or is otherwise removed.

15. The material released from the catheter heads of the embodiments of FIGS. 1-3 and 5 may comprise miniature containers of a microelectronic circuit, a battery and one or more sensors adapted to be disposed, as described, at a selected location within the body or body duct and to operate thereafter, either continuously or periodically, to sense or detect one or more physiological variables and to transmit data as short wave signals to a receiver outside of the body indicative of such variable(s).

I claim:

1. A catheter comprising:
an elongated hollow flexible tubular member adapted to be inserted into and moved along a body duct, such as an artery,
an operating head attached to and terminating at one end of said flexible tubular member and having a side wall portion facing lateral to the longitudinal axis of said flexible tubular member,
an elongated narrow passageway extending longitudinally and laterally through said operating head and terminating at one end at an opening in said side wall of said head,
a hollow hypodermic needle having a dispensing front end with an opening therein, said needle being completely disposed and supported within said operating head and movable longitudinally through said passageway in said head from a retracted position therein whereby the dispensing end of said needle is below said opening in said side wall of said head to an extended position whereby said dispensing end of said needle projects laterally outwardly beyond the side wall of said head so as to permit said dispensing end of said needle to penetrate tissue against the side wall of said head,
first means at the other end of said elongated hollow flexible tubular member for applying a force for urging movement of said needle through said passageway in said head from said retracted position therein to said extended position lateral of said head and for returning said needle from said extended to said retracted position within said head when said head is selectively located within a passageway of a living being, second means for introducing a liquid into said needle and ejecting said liquid through the opening in the dispensing end of said needle into tissue penetrated by the end of said needle.

2. A catheter in accordance with claim 1 wherein said second means for introducing a liquid into said needle is coupled to force said liquid through said hollow flexible tube, said hypodermic needle having a second opening therein extending to the exterior of said needle a distance from said first opening at the dispensing end of said needle, said second opening being in coupling communication with the interior of said flexible tube connected to said head to permit liquid introduced into said tube under pressure to flow through said needle and to be ejected from the dispensing end of said needle.

3. A catheter in accordance with claim 1 wherein said means urging movement of said needle comprises an elongated flexible shaft extending through said flexible tube with one end of said flexible shaft operable connected to said needle and means at the other end of said shaft for urging back and forth longitudinal movement of said shaft through said flexible tube to cause the forward and reverse travel of said needle through said passageway in said head.

4. A catheter in accordance with claim 1 wherein said means for urging movement of said needle through said passageway in said head comprises means for generating positive fluid pressure in said flexible tube and transmitting said pressure as a force to urge movement of said needle through said passageway.

5. A catheter in accordance with claim 4 including piston means connected to said needle for receiving the force of the fluid under pressure applied thereto through said flexible tube and for urging movement of said needle through said passageway in said head.

6. A catheter in accordance with claim 1 wherein said means for urging movement of said needle through said passageway in said head comprises a piston operatively connected to said needle, a bore extending partly through said head coupled to said passageway containing said needle, said piston being slidably movable within said bore and operable to receive the force of fluid pressure generated within fluid disposed within said flexible tube and to move back and forth within said bore in accordance with the fluid pressure applied thereto.

7. A catheter comprising:

an elongated hollow tubular member adapted to be inserted into and moved along a body duct, such as an artery, an operating head attached to and terminating at one end of said flexible tube and having a side wall portion facing lateral to the longitudinal axis of said flexible tube, an elongated narrow passageway extending longitudinally and laterally through said head and terminating at one end thereof at an opening in said side wall of said head, a hollow hypodermic needle having a dispensing front end with an opening therein, said needle being supported within and movable longitudinally through said passageway from a retracted position whereby the dispensing end of said needle is below said opening in said side wall of said head to an extended position whereby said dispensing end of said needle projects laterally outwardly beyond the side wall of said head to permit said dispensing end of said needle to penetrate tissue disposed adjacent the side wall of said head, a piston secured to said needle, first means at the other end of said elongated hollow flexible tubular member for generating positive fluid pressure in said flexible tubular member and for applying said fluid pressure to said piston to urge movement of said needle from said retracted to said extended position and means for urging movement of said needle from said extended to said retracted position within said head when said head is selectively located within a living being, and second means for introducing a liquid into said needle and ejecting said liquid through the opening in said dispensing end of said needle.

8. A catheter comprising:

an elongated hollow flexible tubular member adapted to be inserted into and moved along a body duct, such as an artery, an operating head attached to and terminating at one end of said flexible tubular member and having a side wall portion facing lateral to the longitudinal axis of said tubular member, an elongated narrow passageway extending longitudinally and laterally through said operating head and terminating at one end at an opening in said side wall of said head, a hollow hypodermic needle having a dispensing front end with an opening therein, said needle being supported within and movable longitudinally through said passageway from a retracted position whereby the dispensing end of said needle is below said opening in said side wall of said head to an extended position whereby said dispensing end of said needle projects laterally outwardly beyond the side wall of said head so as to permit said dispensing end of said needle to penetrate tissue adjacent the side wall of said head, a bore extending partly through said operating head, a piston operatively connected to said needle and communicating with said passageway containing said needle, said piston being slidably movable within said bore, first means at the other end of said elongated hollow flexible tubular member for generating positive fluid pressure in said flexible tubular member and for applying said fluid pressure to said piston so as to urge movement of said needle from said retracted to said extended position and means for returning said needle from said extended to said retracted position within said head when said head is selectively located within a living being, and second means for introducing a liquid into said needle and ejecting said liquid through the opening in the dispensing end of said needle.

* * * * *